United States Patent [19]
Ouchi

[11] Patent Number: 6,162,221
[45] Date of Patent: Dec. 19, 2000

[54] DRAINAGE TUBE INTRODUCER FOR ENDOSCOPE

[75] Inventor: Teruo Ouchi, Saitama, Japan

[73] Assignee: Asahi Kogaku Kogyo Kabushiki Kaisha, Tokyo, Japan

[21] Appl. No.: 09/168,853

[22] Filed: Oct. 9, 1998

[30] Foreign Application Priority Data

| Oct. 29, 1997 | [JP] | Japan | 296525 |
| Oct. 29, 1997 | [JP] | Japan | 9-296783 |
| Oct. 29, 1997 | [JP] | Japan | 9-296784 |
| Jul. 23, 1998 | [JP] | Japan | 10-207292 |
| Jul. 23, 1998 | [JP] | Japan | 10-207292 |

[51] Int. Cl.[7] .................................. A61B 18/14
[52] U.S. Cl. ..................... 606/49; 606/46; 604/21; 604/114; 604/164; 604/171
[58] Field of Search ................. 606/45, 46, 49; 604/22, 114, 164, 171, 239, 21; 600/585

[56] References Cited

U.S. PATENT DOCUMENTS 4,708,137 11/1987 Tsukagoshi ........................ 606/46
5,840,015 11/1998 Ogino.

FOREIGN PATENT DOCUMENTS 57-99941 6/1982 Japan.
9-103433 4/1997 Japan.

*Primary Examiner*—Lee Cohen
*Attorney, Agent, or Firm*—Greenblum & Bernstein, P.L.C.

[57] ABSTRACT

A drainage tube introducer for an endoscope includes an electrically conductive exposed portion provided on the outer surface of a part at the distal end of a drainage tube guide wire that is stabbed into the inner wall of a body cavity. An electric current conducting device is disposed in a sheath of the drainage tube guide wire to supply an electric current for cauterization to the electrically conductive exposed portion from the proximal end of the sheath.

17 Claims, 19 Drawing Sheets

DRAINAGE TUBE INTRODUCER FOR ENDOSCOPE

BACKGROUND OF THE INVENTION

The present disclosure relates to subject matter contained in Japanese Patent Application No. 9-296525 (filed on Oct. 29, 1997), Japanese Patent Application No. 9-296783 (filed on Oct. 29, 1997), Japanese Patent Application No. 9-296784 (filed on Oct. 29, 1997) and Japanese Patent Application No. 10-207292 (filed on Jul. 23, 1998), which are expressly incorporated herein by reference in their entireties.

1. Field of the Invention

The present invention relates to a drainage tube introducer for an endoscope that is used through an instrument-inserting channel of the endoscope to introduce a drainage tube into a body cavity for the purpose of draining (through-draining) a narrow part in the body cavity.

2. Description of the Prior Art

To draw accumulated pancreatic juice from the pancreas or the pancreatic duct into the stomach, a technique uses a drainage tube introducer for an endoscope that has a drainage tube guide wire removably inserted therein. The drainage tube introducer is passed through an instrument-inserting channel of an endoscope (particularly, an ultrasonic endoscope) to puncture the pancreas from the inner wall of the stomach.

Thereafter, with the distal end of the drainage tube guide wire left in the pancreatic duct, the drainage tube introducer is drawn out of the patient's body. Then, a drainage tube is inserted into the pancreatic duct by passing it over the drainage tube guide wire. Finally, the drainage tube guide wire is drawn out of the patient's body, thereby enabling the drainage tube to be left under the conditions that one end of the drainage tube opens into the pancreatic duct, and the other end opens into the stomach.

A general drainage tube introducer used in the above-described procedure has a wire guide tube that has a distal end formed in the shape of a syringe needle. The wire guide tube is arranged to allow the drainage tube guide wire to be removably inserted therein over the entire length thereof. The wire guide tube is axially movably inserted in a sheath that is removably inserted into an instrument-inserting channel of an endoscope.

Incidentally, it is not easy for the drainage tube introducer to reach the pancreatic duct from the inner wall of the stomach because it must be stabbed to a considerable depth against great resistance. Furthermore, the drainage tube introducer may damage a blood vessel in the depths that cannot be seen from the surface. Because bleeding in the depths cannot be observed through an endoscope, there are many cases where the operator cannot be free from anxiety when performing a treatment using the drainage tube introducer.

SUMMARY OF THE INVENTION

An object of the present invention is to provide a drainage tube introducer for an endoscope that can be readily stabbed as far as a deep part without likelihood of bleeding from the punctured part, thus allowing a drainage tube to be safely introduced into the body cavity.

Other objects and advantages of the present invention will become apparent from the following detailed description of illustrated embodiments of the invention.

According to the present invention, there is provided a drainage tube introducer for an endoscope that has a sheath removably inserted into an instrument-inserting channel of the endoscope. A drainage tube guide wire is axially movably and removably inserted in the sheath. The distal end portion of the drainage tube guide wire is projected from and withdrawn into the distal end of the sheath by an operation conducted at the proximal end of the sheath, so that the projected distal end portion of the drainage tube guide wire is stabbed into the inner wall of a body cavity. The drainage tube introducer includes an electrically conductive exposed portion provided on the outer surface of a part adapted to be stabbed into the inner wall of the body cavity. The electrically conductive exposed portion is formed from an electrically conductive material. The drainage tube introducer further includes an electric current conducting device provided in the sheath to supply an electric current for cauterization to the electrically conductive exposed portion from the proximal end of the sheath.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
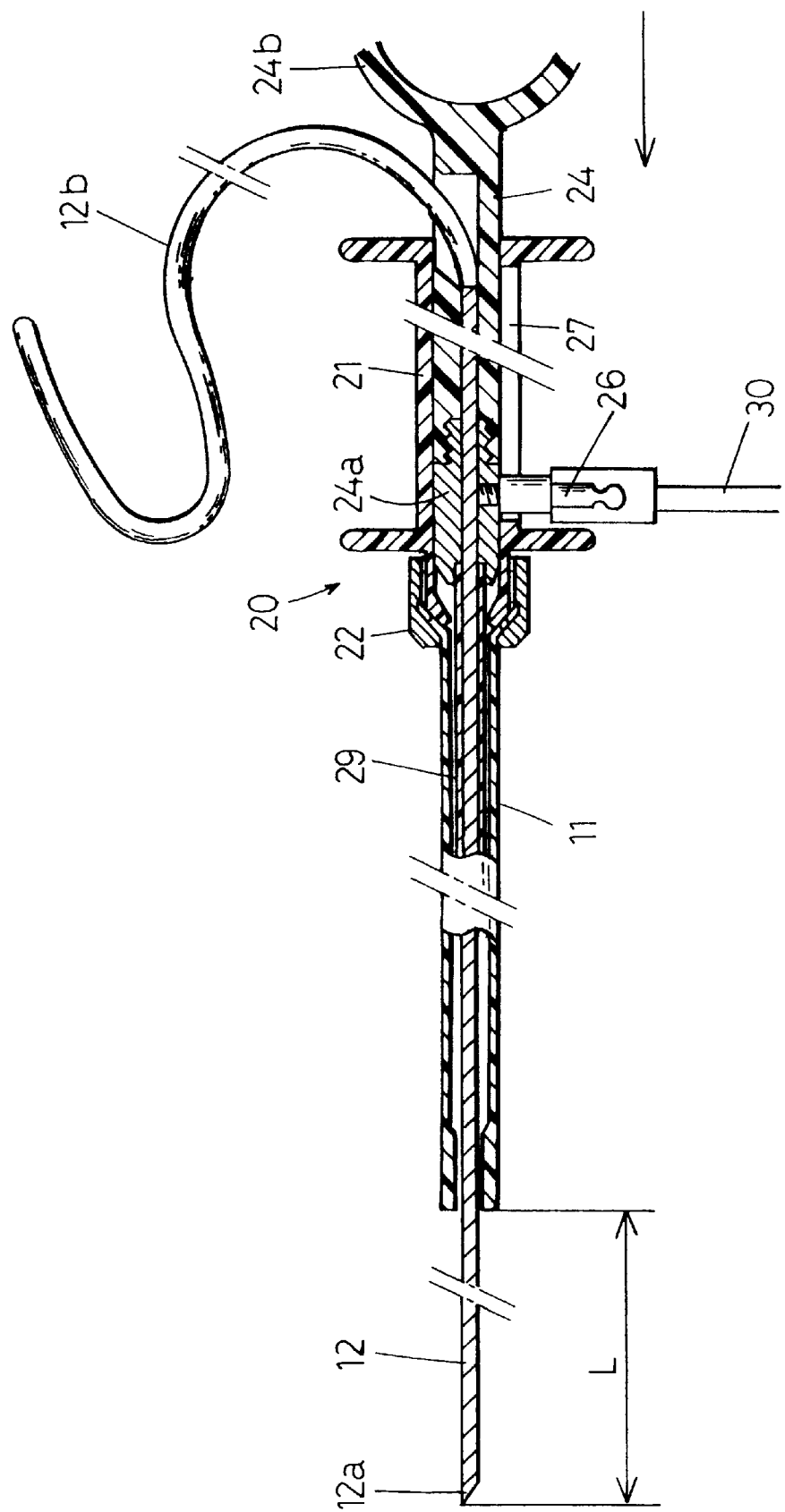
FIG. 1 is a sectional side view of a drainage tube introducer for an endoscope according to a first embodiment of the present invention, showing a state wherein a distal end portion of a drainage tube guide wire projects from the distal end of a sheath.
Figure 2:
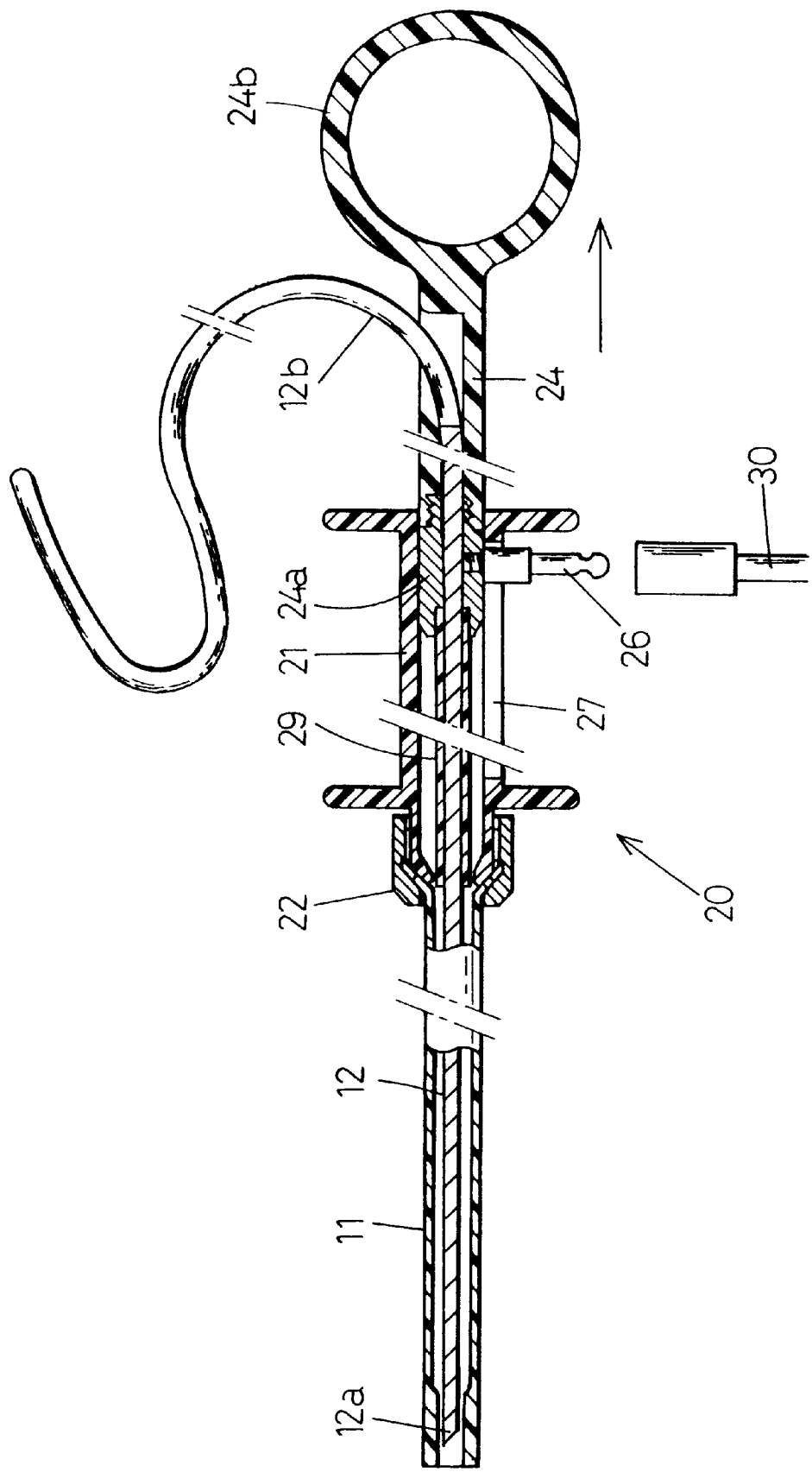
FIG. 2 is a sectional side view of the drainage tube introducer according to the first embodiment of the present invention, showing a state wherein the distal end portion of the drainage tube guide wire is withdrawn into the distal end of the sheath.

FIG. 1 shows a drainage tube introducer for an endoscope according to a first embodiment of the present invention in a state where the distal end of a drainage tube guide wire 12 projects from the distal end of a sheath 11. FIG. 2 shows the drainage tube introducer in a state where the distal end of the drainage tube guide wire 12 is withdrawn into the distal end of the sheath 11.

The sheath 11 is adapted to be removably inserted into an instrument-inserting channel of an endoscope (not shown). The sheath 11 is formed from an electrically insulating flexible tube, for example, a tetrafluoroethylene resin tube.

The drainage tube guide wire 12 is axially movably and removably inserted in the sheath 11 over the entire length of the sheath 11. The drainage tube guide wire 12 is adapted to guide a drainage tube (not shown). The drainage tube guide wire 12 is a flexible stranded wire formed by twisting together electrically conductive metal small-gage wires. Alternatively, the drainage tube guide wire 12 may be formed from a single small-gage wire of an electrically conductive metal.

The drainage tube guide wire 12 has nothing attached to either end thereof. A distal end portion 12a of the drainage tube guide wire 12 is diagonally cut in the shape of a needle. In the case of a stranded wire, the strands are brazed together at the distal end portion 12a by silver brazing or the like. The overall length of the drainage tube guide wire 12 is at least double the overall length of the sheath 11.

An operating part 20 is connected to the proximal (rear) end of the sheath 11. The operating part 20 has a body 21 formed from an electrically insulating plastic material. The proximal end of the sheath 11 is secured to the operating part body 21 by a retaining nut 22 screwed onto the distal end portion of the operating part body 21.

A guide wire slider 24 is slidably fitted in a through-bore provided in the axial position of the operating part body 21. A connecting member 24a is secured by thread engagement to the distal end portion of the guide wire slider 24 in the operating part body 21. The connecting member 24a is made of an electrically conductive metal.

The guide wire slider 24, exclusive of the connecting member 24a, is formed from an electrically insulating plastic material. A ring-shaped finger engagement portion 24b is formed at an end of the guide wire slider 24 projecting from the operating part body 21 so that the operator's thumb is engageable with the finger engagement portion 24b.

The proximal half of the drainage tube guide wire 12 extends outside from the guide wire slider 24. The outer surface of the proximal half of the drainage tube guide wire 12 is provided with electrically insulating covering 12b, e.g. tetrafluoroethylene resin coating.

A connecting terminal 26 is screwed into a side portion of the guide wire slider 24 to project sideways. The connecting terminal 26 is connected to a high-frequency power supply cord 30 of a high-frequency power supply for cauterization (not shown).

More specifically, the connecting terminal 26 is screwed into the metallic connecting member 24a to press an intermediate portion of the drainage tube guide wire 12 with an end surface thereof, thereby mechanically securing the drainage tube guide wire 12 to the connecting member 24a. Consequently, the connecting terminal 26 and the drainage tube guide wire 12 are electrically connected to each other directly and through the connecting member 24a.

If the connecting terminal 26 screwed into the connecting member 24a is untightened, the drainage tube guide wire 12 is unlocked from the connecting member 24a, and it becomes possible to move the drainage tube guide wire 12 back and forth relative to the guide wire slider 24 and the sheath 11.

A slit 27 is formed in a side wall portion of the operating part body 21 in parallel to the axis of the operating part body 21 to allow the connecting terminal 26 to extend through and move along the slit 27. The slit 27 limits a maximum movable range in the axial direction of the guide wire slider 24.

A reinforcing pipe 29 is provided to surround the drainage tube guide wire 12 to prevent buckling of the drainage tube guide wire 12, for which there is a rather wide free space in the operating part body 21.

With the drainage tube introducer arranged as stated above, the operator holds the operating part body 21 and actuates the guide wire slider 24 to move axially relative to the operating part body 21. By doing so, the distal end portion 12a of the drainage tube guide wire 12 can be projected from and withdrawn into the distal end of the sheath 11. The maximum projection length L of the distal end portion 12a is of the order of from 5 centimeters to 12 centimeters, for example.

If the high-frequency power supply cord 30 is connected to the connecting terminal 26, a high-frequency electric current for cauterization can be supplied to the distal end portion 12a of the drainage tube guide wire 12 projecting from the distal end of the sheath 11.

Because the sheath 11 is formed from an electrically insulating material, there is no leakage of electric current to the outer surface. The portion of the drainage tube guide wire 12 that extends rearward from the guide wire slider 24 is also provided with the electrically insulating covering 12b. Therefore, there is no leakage of electric current to the outer surface of the externally extending portion of the drainage tube guide wire 12.

Figure 3:
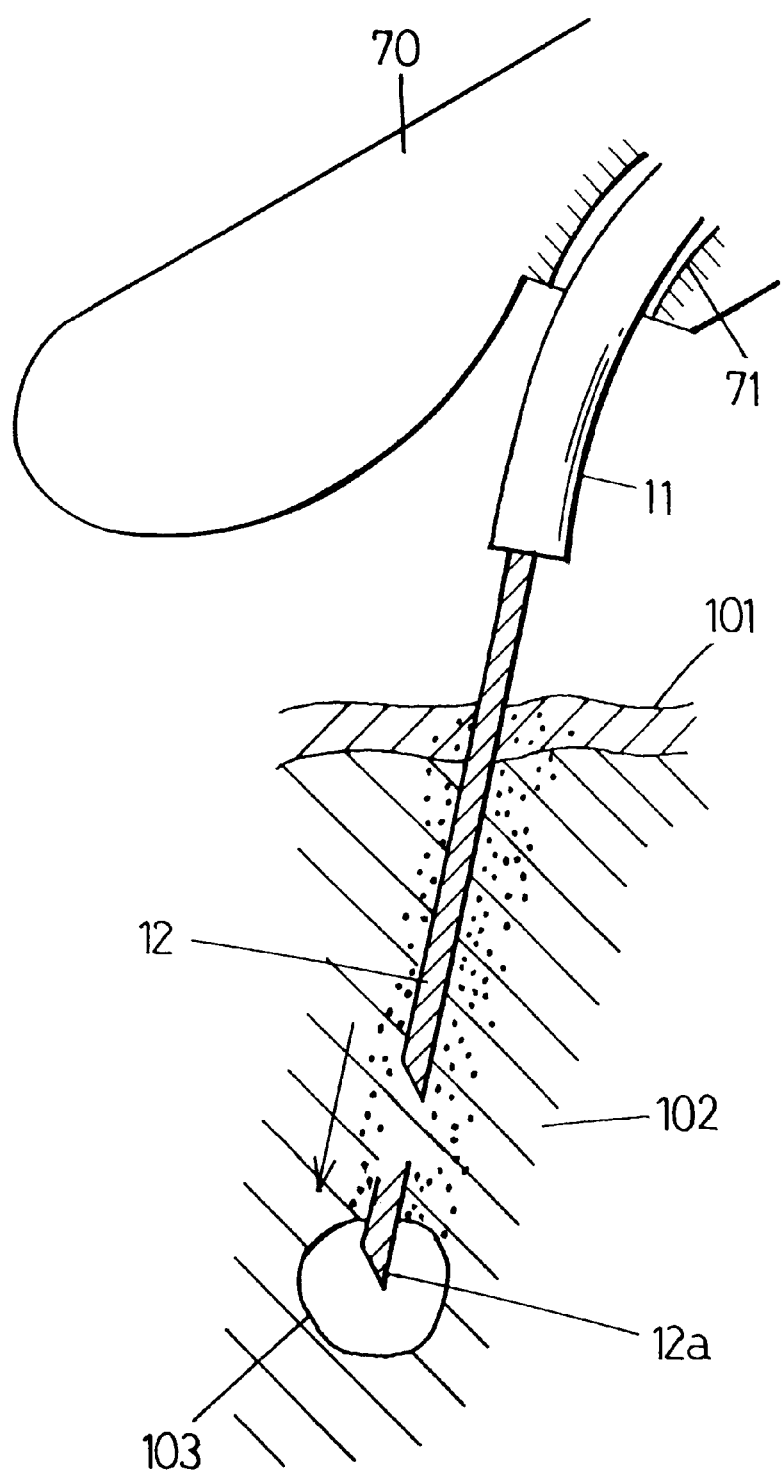
FIG. 3 is a diagram schematically showing the way in which the drainage tube introducer according to the first embodiment of the present invention is actually used.

The above-described drainage tube introducer according to the embodiment is used as follows. First, as shown in FIG. 3, the drainage tube introducer is passed through an instrument-inserting channel 71 of an ultrasonic endoscope 70. Then, the respective positions of the pancreas 102 and the pancreatic duct 103 are confirmed by jointly using optical observation and ultrasonic tomographic observation. While doing so, the operator punctures the pancreas 102 with the drainage tube guide wire 12 from the stomach mucous membrane 101, aiming at the pancreatic duct 103.

During the puncture treatment, a high-frequency electric current is passed through the drainage tube guide wire 12. Consequently, organic tissues touching the surface of the drainage tube guide wire 12 are cauterized and coagulated. Therefore, the puncture can be readily performed, and bleeding is prevented.

When the distal end portion 12a of the drainage tube guide wire 12 has reached a position in the pancreatic duct 103, the screwed connecting terminal 26 is untightened. Then, the sheath 11, together with the operating part body 21, is drawn out to the proximal end of the drainage tube guide wire 12 and removed therefrom, with only the drainage tube guide wire 12 left as it is.

Figure 4:
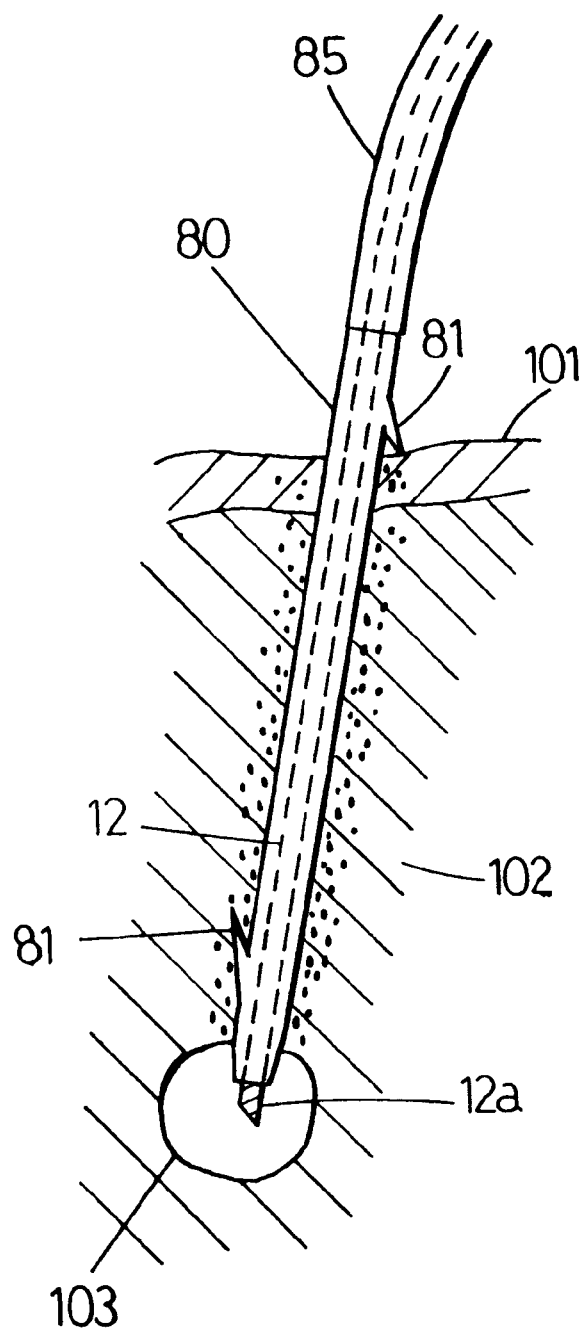
FIG. 4 is a diagram schematically showing the way in which the drainage tube introducer according to the first embodiment of the present invention is actually used.

Then, as shown in FIG. 4, a drainage tube 80 is pushed with a pusher 85 by using the drainage tube guide wire 12 as a guide. The pusher 85 is formed from a flexible tube. The drainage tube 80 is a flexible plastic tube having a pair of barbs 81 to prevent the drainage tube 80 from dislodging or undesirably going into the depths.

When the drainage tube 80 has been positioned such that two ends thereof open into the pancreatic duct 103 and the stomach, respectively, the pusher 85 and the drainage tube guide wire 12 are drawn out of the patient's body. Consequently, the drainage tube 80 is solely left in the body cavity to draw pancreatic juice into the stomach.

Figure 5:
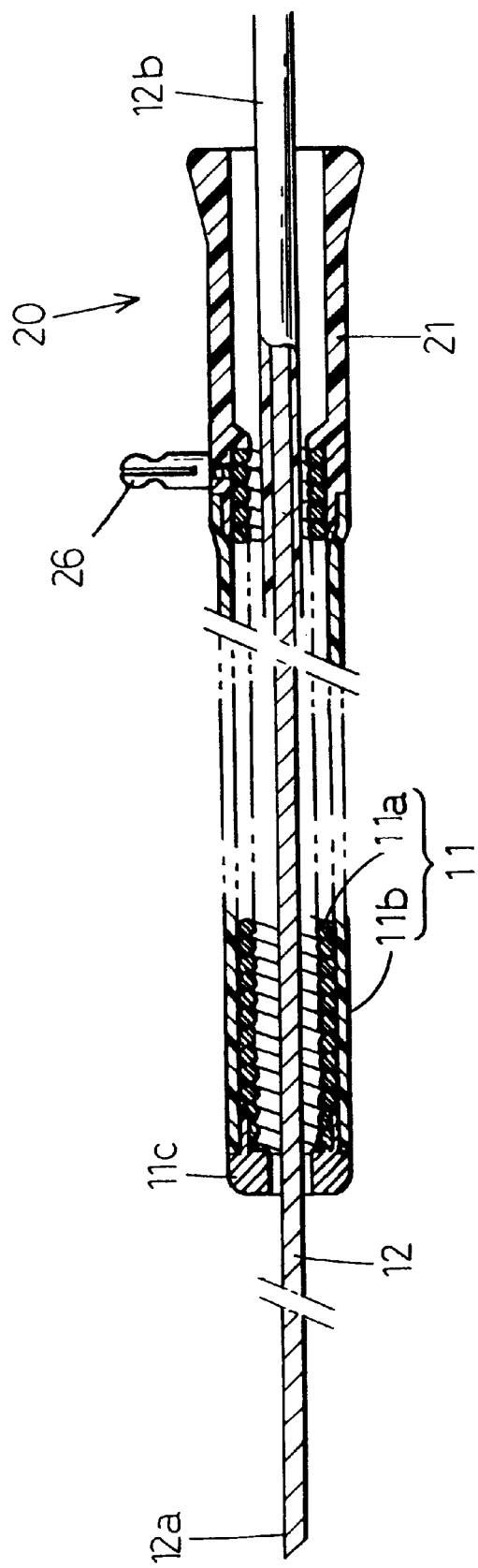
FIG. 5 is a sectional side view of a drainage tube introducer for an endoscope according to a second embodiment of the present invention, showing a state wherein a distal end portion of a drainage tube guide wire projects from the distal end of a sheath.

FIG. 5 shows a drainage tube introducer for an endoscope according to a second embodiment of the present invention. A sheath 11 has a coil pipe 11a formed by close-winding an electrically conductive metal wire, e.g. a stainless steel wire, into a helical shape with a uniform diameter. The outer surface of the coil pipe 11a is covered with a flexible electrically insulating tube 11b, e.g. a tetrafluoroethylene resin tube.

A distal end tip 11c is secured to the distal end of the sheath 11. The distal end tip 11c is made of an electrically conductive metal, e.g. a stainless steel. The distal end tip 11c is connected to the distal end portion of the coil pipe 11a by silver brazing or soldering, for example. Thus, the distal end tip 11c and the coil pipe 11a are electrically connected to each other.

An operating part 20 is provided with only an operating part body 21 that is an electrically insulating member formed in a cylindrical shape. The operating part is arranged such that the operator moves the drainage tube guide wire 12 back and forth with his/her fingers directly.

A connecting terminal 26 is screwed into a side portion of the operating part body 21. The distal end of the connecting terminal 26 is in contact with the coil pipe 11a of the sheath 11, so that a high-frequency electric current is supplied from the connecting terminal 26 to the coil pipe 11a and the distal end tip 11c.

The overall length of the drainage tube guide wire 12 is at least double the overall length of the sheath 11. A portion of the drainage tube guide wire 12 that extends rearward from the operating part body 21 is provided with an insulating covering 12b, which is either an electrically insulating tube or coating of a tetrafluoroethylene resin material, for example.

During use of the above-described drainage tube introducer according to the second embodiment, some portion of the coil pipe 11a of the sheath 11 and the distal end tip 11c invariably touches the drainage tube guide wire 12. Therefore, a high-frequency electric current can be supplied to the distal end portion 12a of the drainage tube guide wire 12 from the connecting terminal 26. The drainage tube introducer is used by following the same procedure as in the case of the first embodiment.

Figure 6:
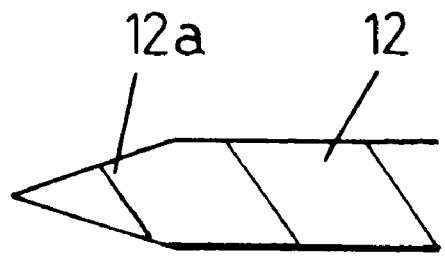
FIG. 6 is a side view showing another example of the shape of the distal end of the drainage tube guide wire according to the first and second embodiments of the present invention.
Figure 7:
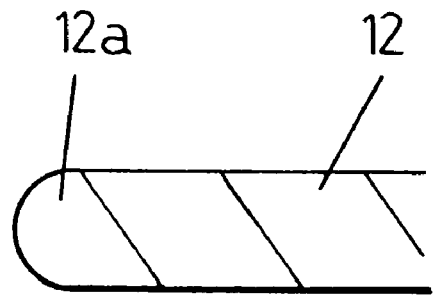
FIG. 7 is a side view showing still another example of the shape of the distal end of the drainage tube guide wire according to the first and second embodiments of the present invention.

It should be noted that the distal end portion 12a of the drainage tube guide wire 12 may be sharpened in a conical shape as shown in FIG. 6. Alternatively, the distal end portion 12a may be rounded in a hemispherical shape as shown in FIG. 7. In other words, the distal end portion 12a may have any appropriate shape.

Figure 8:
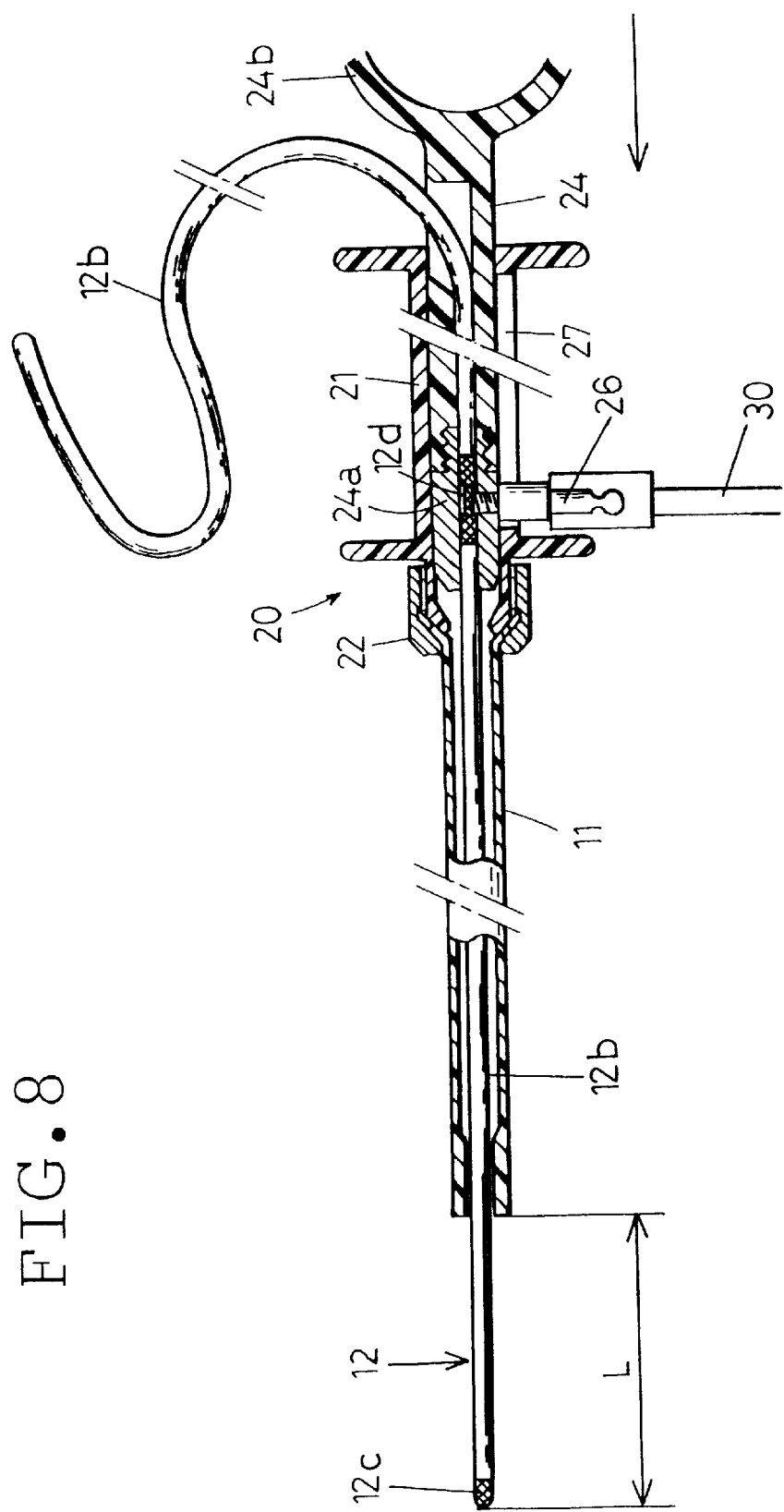
FIG. 8 is a sectional side view of a drainage tube introducer for an endoscope according to a third embodiment of the present invention, showing a state wherein a distal end portion of a drainage tube guide wire projects from the distal end of a sheath.
Figure 9:
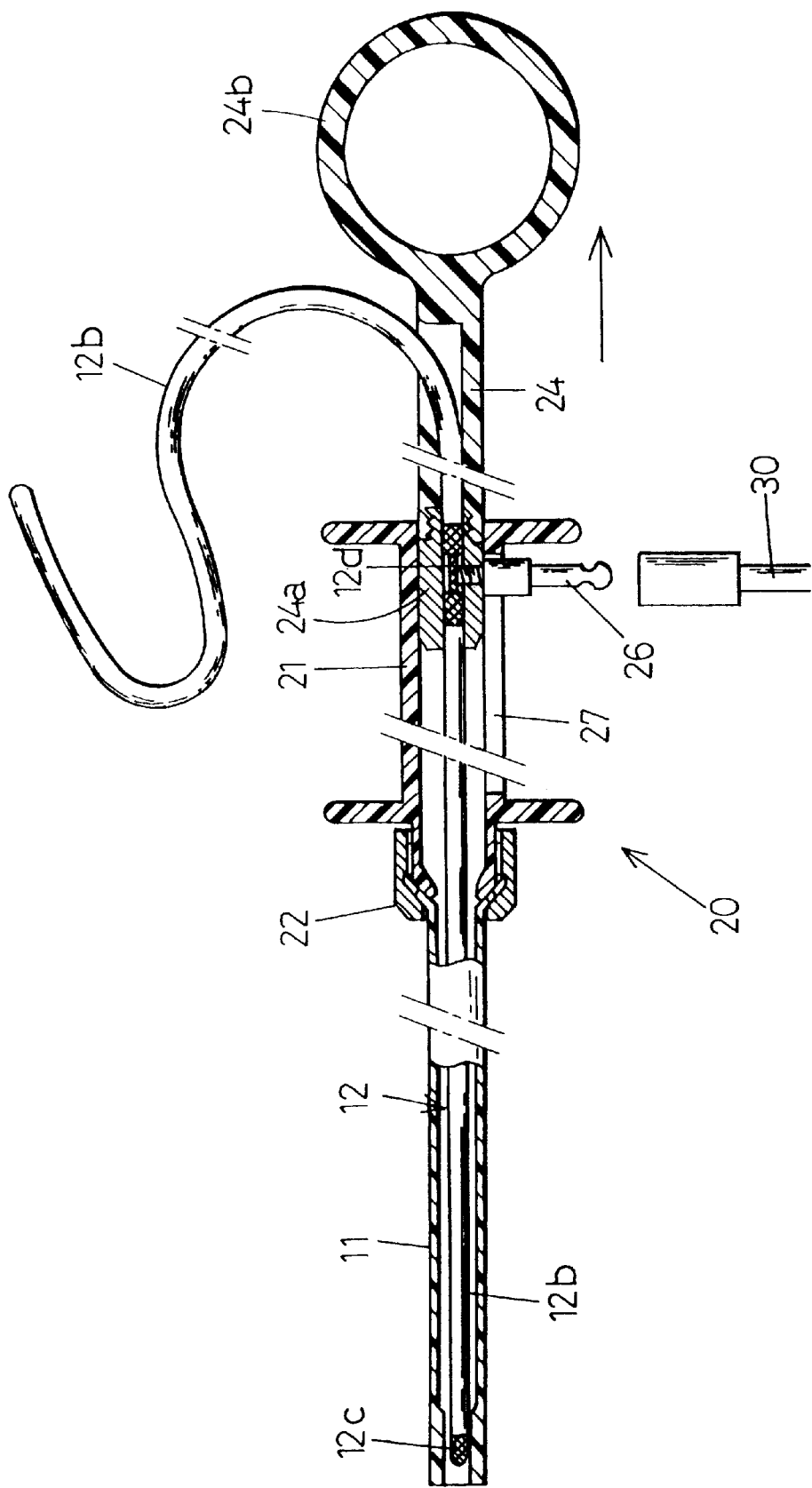
FIG. 9 is a sectional side view of the drainage tube introducer according to the third embodiment of the present invention, showing a state wherein the distal end portion of the drainage tube guide wire is withdrawn into the distal end of the sheath.

FIG. 8 shows a drainage tube introducer for an endoscope according to a third embodiment of the present invention in a state where the distal end of a drainage tube guide wire 12 projects from the distal end of a sheath 11. FIG. 9 shows the drainage tube introducer in a state where the distal end of the drainage tube guide wire 12 is withdrawn into the distal end of the sheath 11.

The sheath 11 is adapted to be removably inserted into an instrument-inserting channel of an endoscope (not shown). The sheath 11 is formed from an electrically insulating flexible tube, for example, a tetrafluoroethylene resin tube.

The drainage tube guide wire 12 is axially movably and removably inserted in the sheath 11 over the entire length of the sheath 11. The drainage tube guide wire 12 is adapted to guide a drainage tube (not shown). The overall length of the drainage tube guide wire 12 is at least double the overall length of the sheath 11.

Figure 10:
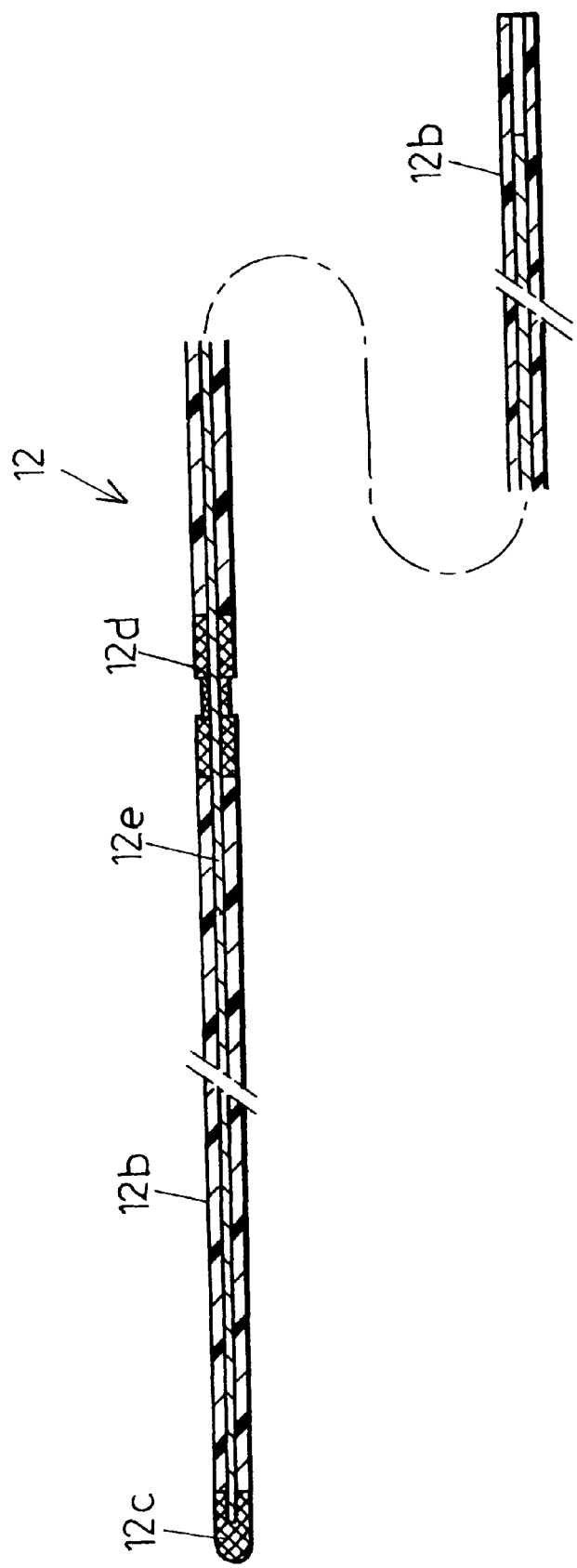
FIG. 10 is a sectional side view of the drainage tube guide wire according to the third embodiment of the present invention.

As shown in FIG. 10, the drainage tube guide wire 12 according to this embodiment is formed from an electrically conductive wire 12e that is a flexible stranded wire formed by twisting together electrically conductive metal small-gage wires. Alternatively, the electrically conductive wire 12e may be a single wire of an electrically conductive metal. The outer surface of the electrically conductive wire 12e is covered with an electrically insulating covering 12b, e.g. a tetrafluoroethylene resin tube, a polyimide resin tube, or a polyethylene resin tube, over substantially the entire length of the electrically conductive wire 12e. At the rear end (right end as viewed in the figure) in particular, the insulating covering 12b extends longer than the electrically conductive wire 12e so that the electrically conductive wire 12e is not exposed.

A distal end electrode 12c made of an electrically conductive metal is disposed at the distal end of the drainage tube guide wire 12. The distal end electrode 12c is exposed to the outside and connected to the electrically conductive wire 12e by silver brazing or soldering, for example.

Figure 11:
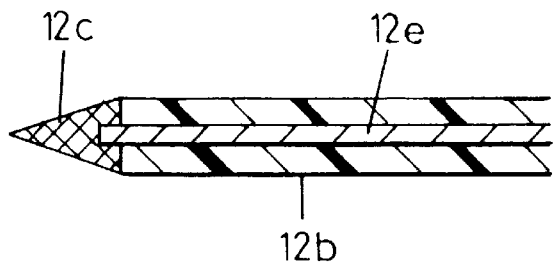
FIG. 11 is a side view showing another example of the shape of the distal end of the drainage tube guide wire according to the third embodiment of the present invention.
Figure 12:
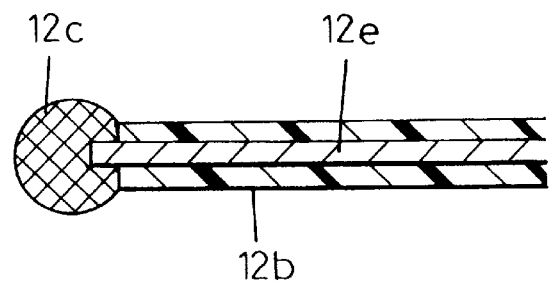
FIG. 12 is a side view showing still another example of the shape of the distal end of the drainage tube guide wire according to the third embodiment of the present invention.

In this embodiment, the distal end electrode 12c is formed in the shape of a bullet with a hemispherical end. However, the distal end electrode 12c may have a conical shape with a pointed end as shown in FIG. 11. Alternatively, the distal end electrode 12c may have a spherical shape as shown in FIG. 12. In other words, the distal end electrode 12c may have any appropriate shape.

Referring to FIG. 10, the drainage tube guide wire 12 has a terminal receiver 12d provided at an intermediate portion thereof that is pressed from a side thereof by the distal end surface of a connecting terminal 26 (described later). The terminal receiver 12d is formed from an electrically conductive metal member.

The terminal receiver 12d is secured to the electrically conductive wire 12e by soldering or silver brazing, for example. Consequently, the terminal receiver 12d and the distal end electrode 12c are electrically connected through the electrically conductive wire 12e. It should be noted that the insulating covering 12b is not provided where the terminal receiver 12d is provided.

Referring to FIGS. 8 and 9, an operating part 20 is connected to the proximal (rear) end of the sheath 11. The operating part 20 has the same structure as the operating part 20 in the first embodiment, which is shown in FIG. 1.

The connecting terminal 26 is screwed into a metallic connecting member 24a. The connecting terminal 26 presses the terminal receiver 12d with its distal end surface, thereby securing the drainage tube guide wire 12 to the connecting member 24a.

Consequently, the connecting terminal 26 and the terminal receiver 12d are electrically connected to each other directly and through the connecting member 24a. In this state, the portion of the drainage tube guide wire 12 that extends rearward from the terminal receiver 12d is longer than the overall length of the sheath 11, and this portion of the drainage tube guide wire 12 extends outside from the guide wire slider 24.

If the connecting terminal 26 screwed into the connecting member 24a is untightened, the drainage tube guide wire 12 is unlocked from the connecting member 24a, and it becomes possible to move the drainage tube guide wire 12 back and forth relative to the guide wire slider 24 and the sheath 11.

If a high-frequency power supply cord 30 is connected to the connecting terminal 26, a high-frequency electric current can be supplied to the distal end electrode 12c at the distal end of the drainage tube guide wire 12 projecting from the distal end of the sheath 11.

Because the sheath 11 is formed from an electrically insulating material, there is no leakage of electric current to the outer surface. The portion of the drainage tube guide wire 12 that extends rearward from the guide wire slider 24 is also provided with the electrically insulating covering 12b. Therefore, there is no leakage of electric current to the outer surface of the externally extending portion of the drainage tube guide wire 12.

Figure 13:
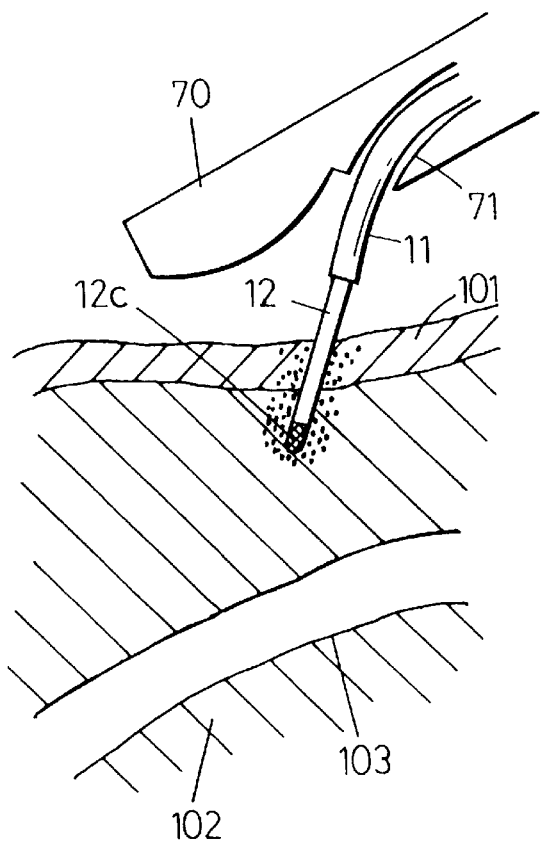
FIG. 13 is a diagram schematically showing the way in which the drainage tube introducer according to the third embodiment of the present invention is actually used.

The above-described drainage tube introducer according to the embodiment is used as follows. First, as shown in FIG. 13, the drainage tube introducer is passed through an instrument-inserting channel 71 of an ultrasonic endoscope 70. Then, the respective positions of the pancreas 102 and the pancreatic duct 103 are confirmed by jointly using optical observation and ultrasonic tomographic observation. While doing so, the operator punctures the pancreas 102 with the drainage tube guide wire 12 from the stomach mucous membrane 101, aiming at the pancreatic duct 103.

During the puncture treatment, a high-frequency electric current is passed through the drainage tube guide wire 12. Consequently, organic tissues touching the surface of the distal end electrode 12c are cauterized and coagulated. Therefore, the puncture can be readily performed, and bleeding is prevented. Cauterization of the organic mucous membrane takes place only at the distal end electrode 12c; the portion that has already been punctured is not uselessly cauterized. Therefore, the safety is improved.

Figure 14:
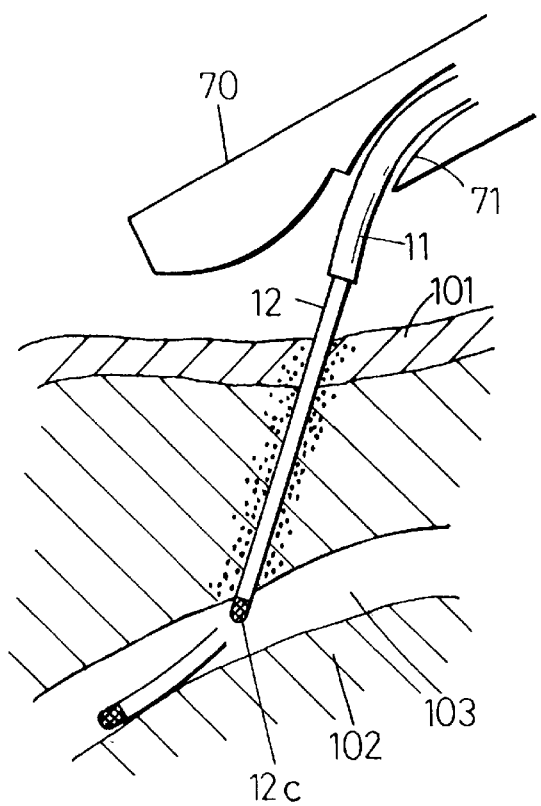
FIG. 14 is a diagram schematically showing the way in which the drainage tube introducer according to the third embodiment of the present invention is actually used.

As shown in FIG. 14, when the distal end electrode 12c of the drainage tube guide wire 12 has reached a position in the pancreatic duct 103, the screwed connecting terminal 26 is untightened. Then, the sheath 11, together with the operating part body 21, is drawn out to the proximal end of the drainage tube guide wire 12 and removed therefrom, with only the drainage tube guide wire 12 left as it is.

Figure 15:
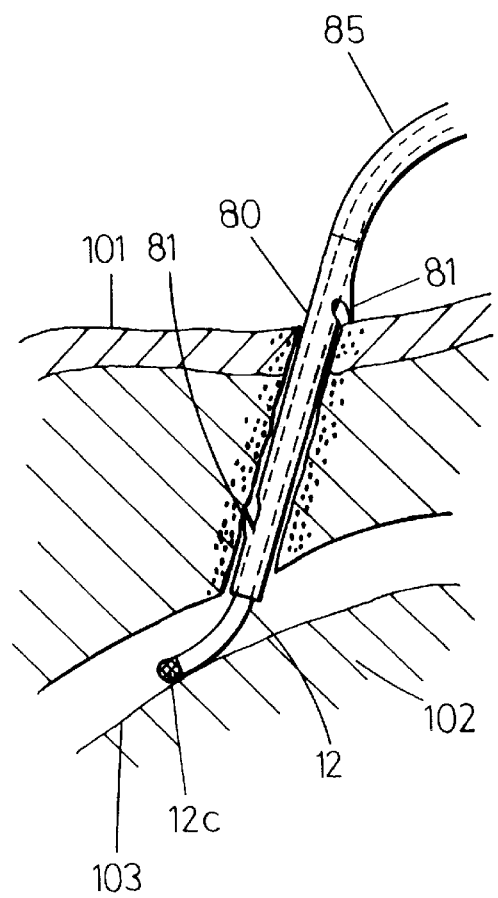
FIG. 15 is a diagram schematically showing the way in which the drainage tube introducer according to the third embodiment of the present invention is actually used.

Then, as shown in FIG. 15, a drainage tube 80 is pushed with a pusher 85 by using the drainage tube guide wire 12 as a guide. The pusher 85 is formed from a flexible tube.

When the drainage tube 80 has been positioned such that two ends thereof open into the pancreatic duct 103 and the stomach, respectively, the pusher 85 and the drainage tube guide wire 12 are drawn out of the patient's body. Consequently, the drainage tube 80 is solely left in the body cavity to draw pancreatic juice into the stomach.

Figure 16:
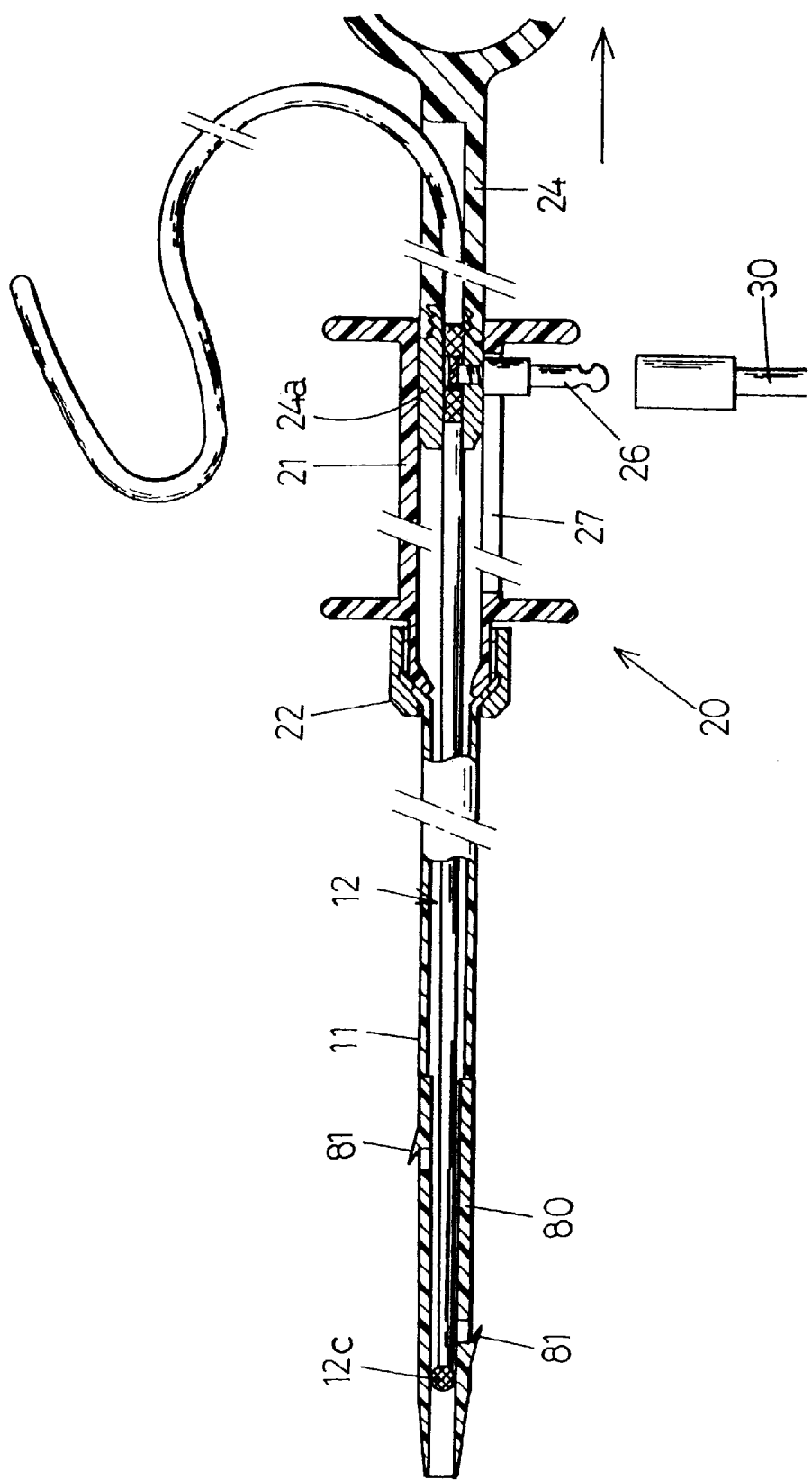
FIG. 16 is a sectional side view of a drainage tube introducer for an endoscope according to a fourth embodiment of the present invention, showing a state wherein a distal end portion of a drainage tube guide wire is withdrawn into the distal end of a sheath.
Figure 17:
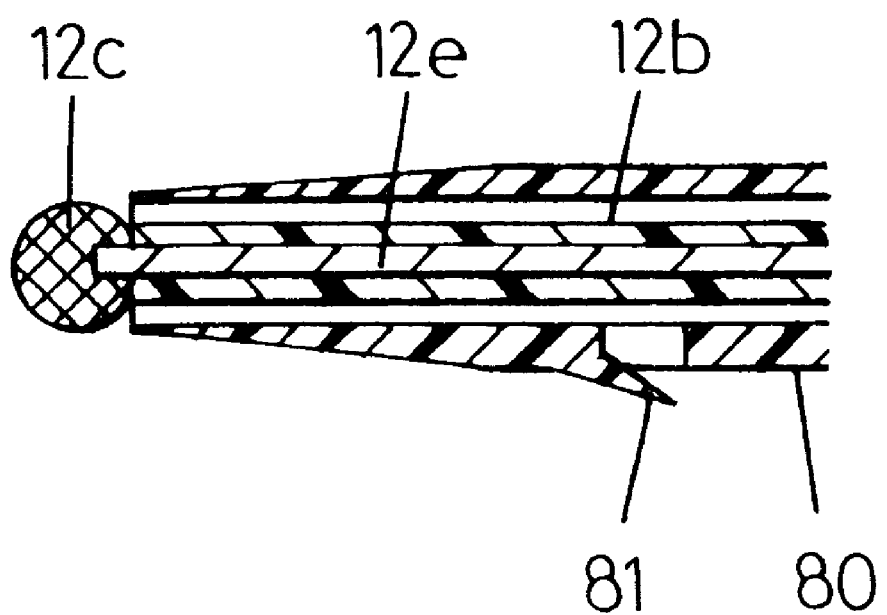
FIG. 17 is a fragmentary enlarged sectional side view of the drainage tube introducer according to the fourth embodiment of the present invention, showing a state wherein the distal end portion of the drainage tube guide wire projects slightly from the distal end of the sheath.

FIGS. 16 and 17 show a drainage tube introducer for an endoscope according to a fourth embodiment of the present invention. In this embodiment, a drainage tube 80 is disposed in series at the distal end of the sheath 11 in the third embodiment, and a drainage tube guide wire 12 is inserted into both the sheath 11 and the drainage tube 80.

FIG. 16 shows the drainage tube introducer in a state where the distal end portion of the drainage tube guide wire 12 is withdrawn into the distal end of the drainage tube 80. FIG. 17 shows the drainage tube introducer in a state where the distal end portion of the drainage tube guide wire 12 projects slightly from the distal end of the drainage tube 80. The distal end portion of the drainage tube 80 is tapered so that it can be readily inserted into the depths of tissues.

With the above-described arrangement, the drainage tube 80 can be left to dwell in a deep part immediately after puncture has been performed with the drainage tube introducer. It should be noted that the outer diameter of the distal end electrode 12c is made slightly larger than the inner diameter of the drainage tube 80 so that the drainage tube 80 is retained by friction between the distal end electrode 12c and the drainage tube 80.

Figure 18:
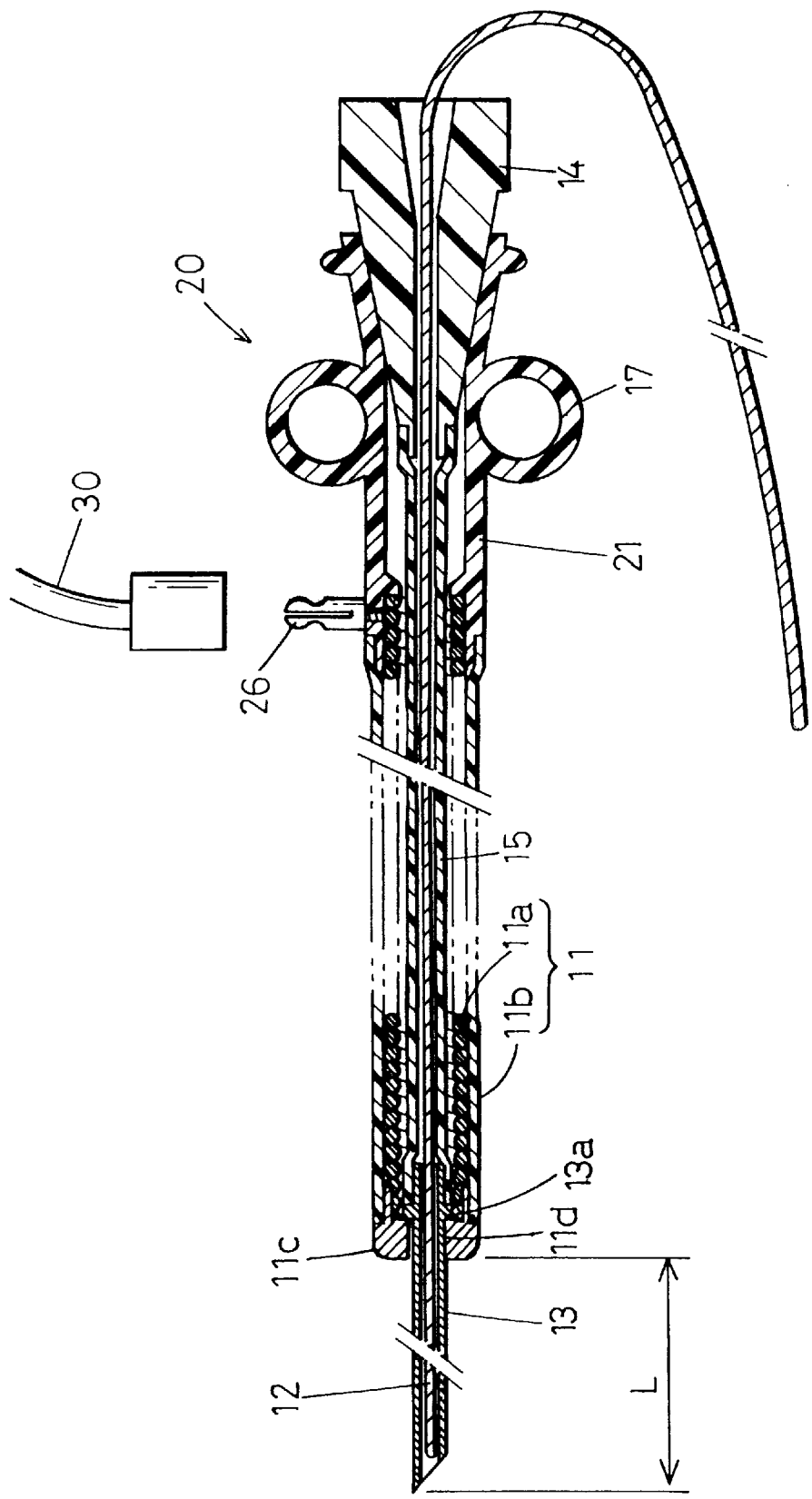
FIG. 18 is a sectional side view of a drainage tube introducer for an endoscope according to a fifth embodiment of the present invention, showing a state wherein a tubular needle as a distal end portion projects from a distal end tip of a sheath.

FIG. 18 shows a drainage tube introducer for an endoscope according to a fifth embodiment of the present invention in a state where a tubular needle 13 is projected from the distal end of a sheath 11.

The sheath 11 is formed as in the case of the second embodiment, which is shown in FIG. 5. That is, the sheath 11 has a coil pipe 11a formed by close-winding an electrically conductive metal wire, e.g. a stainless steel wire, into a helical shape with a uniform diameter. The outer surface of the coil pipe 11a is covered with a flexible electrically insulating tube 11b, e.g. a tetrafluoroethylene resin tube.

A distal end tip 11c is secured to the distal end of the sheath 11. The distal end tip 11c is made of an electrically conductive metal, e.g. a stainless steel. The distal end tip 11c is connected to the distal end portion of the coil pipe 11a by silver brazing or soldering, for example. Thus, the distal end tip 11c and the coil pipe 11a are electrically connected to each other.

Figure 19:
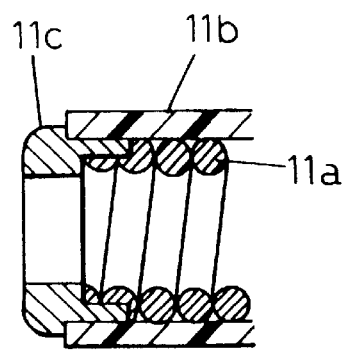
FIG. 19 is a fragmentary sectional side view showing another example of the distal end tip of the sheath according to the fifth embodiment of the present invention.

If the outer diameter of the distal end tip 11c is made smaller than the outer diameter of the sheath 11, as shown in FIG. 19, when the drainage tube introducer is inserted into an instrument-inserting channel of an endoscope, the distal end tip 11c is unlikely to touch a member provided on the endoscope. Accordingly, the safety is further improved. The same is the case with the second embodiment.

An inner tube 15 is axially movably inserted in the sheath 11. The inner tube 15 is an electrically insulating flexible tube such as a tetrafluoroethylene resin tube.

A tubular needle 13 is rigidly connected to the distal end of the inner tube 15. The tubular needle 13 has a syringe needle-like shape and is formed from a stainless steel, for example. By axially moving the inner tube 15 in the sheath 11, the tubular needle 13 is projected from and withdrawn into the distal end of the sheath 11 through a needle passing hole 11d that is formed in the axis position of the distal end tip 11c to extend therethrough.

The tubular needle 13 has a collar 13a formed on the outer peripheral surface of a portion thereof close to the rear end. The collar 13a has a diameter with which it cannot pass through the needle passing hole lid. When the collar 13a abuts on the reverse surface of the distal end tip 11c as shown in FIG. 18, the tubular needle 13 projects from the distal end surface of the distal end tip 11c by a predetermined length but cannot project any further.

A movable tube 14 made of an electrically insulating plastic material is secured to the proximal end of the inner tube 15. The movable tube 14 is axially movable in an operating part body 21 that is made of an electrically insulating material and connected to the proximal end of the sheath 11. Accordingly, by moving the movable tube 14 back and forth relative to the operating part body 21, the tubular needle 13 can be projected from and withdrawn into the distal end of the sheath 11.

The mutually engaging portions of the operating part body 21 and the movable tube 14 are tapered as in the case of those of the syringe tube and needle of a common syringe structure. Accordingly, forcing the movable tube 14 into the operating part body 21 enables these members to be engaged with each other so firmly that the movable tube 14 will not come off easily. The movable tube 14 can be disengaged from the operating part body 21 by pulling it with somewhat strong force. Reference numeral 17 in FIG. 18 denotes finger engagement portions provided on the operating part body 21.

A connecting terminal 26 is provided on a side portion of the operating part body 21. The connecting terminal 26 is connected to a high-frequency power supply cord 30 of a high-frequency power supply (not shown). The connecting terminal 26 is screwed into the operating part body 21. The bottom of the connecting terminal 26 is in contact with the coil pipe 11a.

Accordingly, a high-frequency electric current can be supplied to the tubular needle 13 from the connecting terminal 26 through the coil pipe 11a and the distal end tip 11c. It should be noted that there is no leakage of electric current because the outer surface of the sheath 11 is covered with the electrically insulating tube 11b.

The drainage tube guide wire 12 is a flexible small-gage stranded wire formed by twisting together small-gage metal wires. Alternatively, the drainage tube guide wire 12 may be a simple wire formed from a slightly hard insulating material or the like. The overall length of the drainage tube guide wire 12 is at least double the overall length of the sheath 11. The drainage tube guide wire 12 is removably inserted in the inner tube 15 over the entire length of the latter.

It should be noted that the surface of a portion of the drainage tube guide wire 12 that extends rearward from the operating part 20 is covered with an electrically insulating coating (not shown) or an electrically insulating tube (not shown). The proximal end portion of the electrically insulating tube preferably extends longer than the proximal end portion of the drainage tube guide wire 12.

Figure 20:
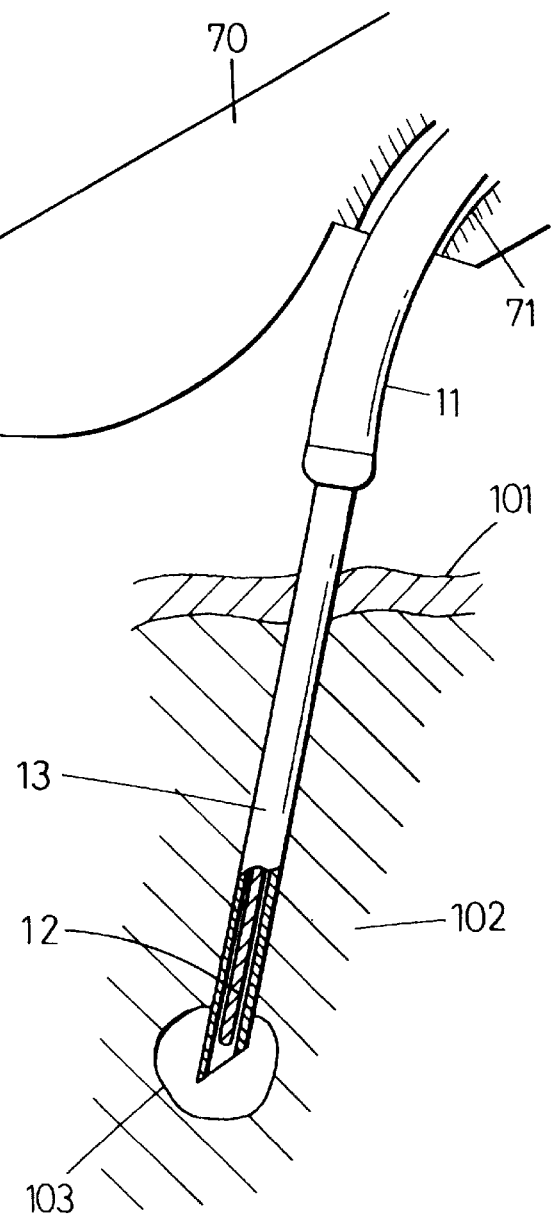
FIG. 20 is a diagram schematically showing the way in which the drainage tube introducer according to the fifth embodiment of the present invention is actually used.

The above-described drainage tube introducer according to the embodiment is used as follows. First, as shown in FIG. 20, the drainage tube introducer is passed through an instrument-inserting channel 71 of an ultrasonic endoscope 70. Then, the respective positions of the pancreas 102 and the pancreatic duct 103 are confirmed by jointly using optical observation and ultrasonic tomographic observation. While doing so, the operator punctures the pancreas 102 with the tubular needle 13 from the stomach mucous membrane 101, aiming at the pancreatic duct 103.

Figure 21:
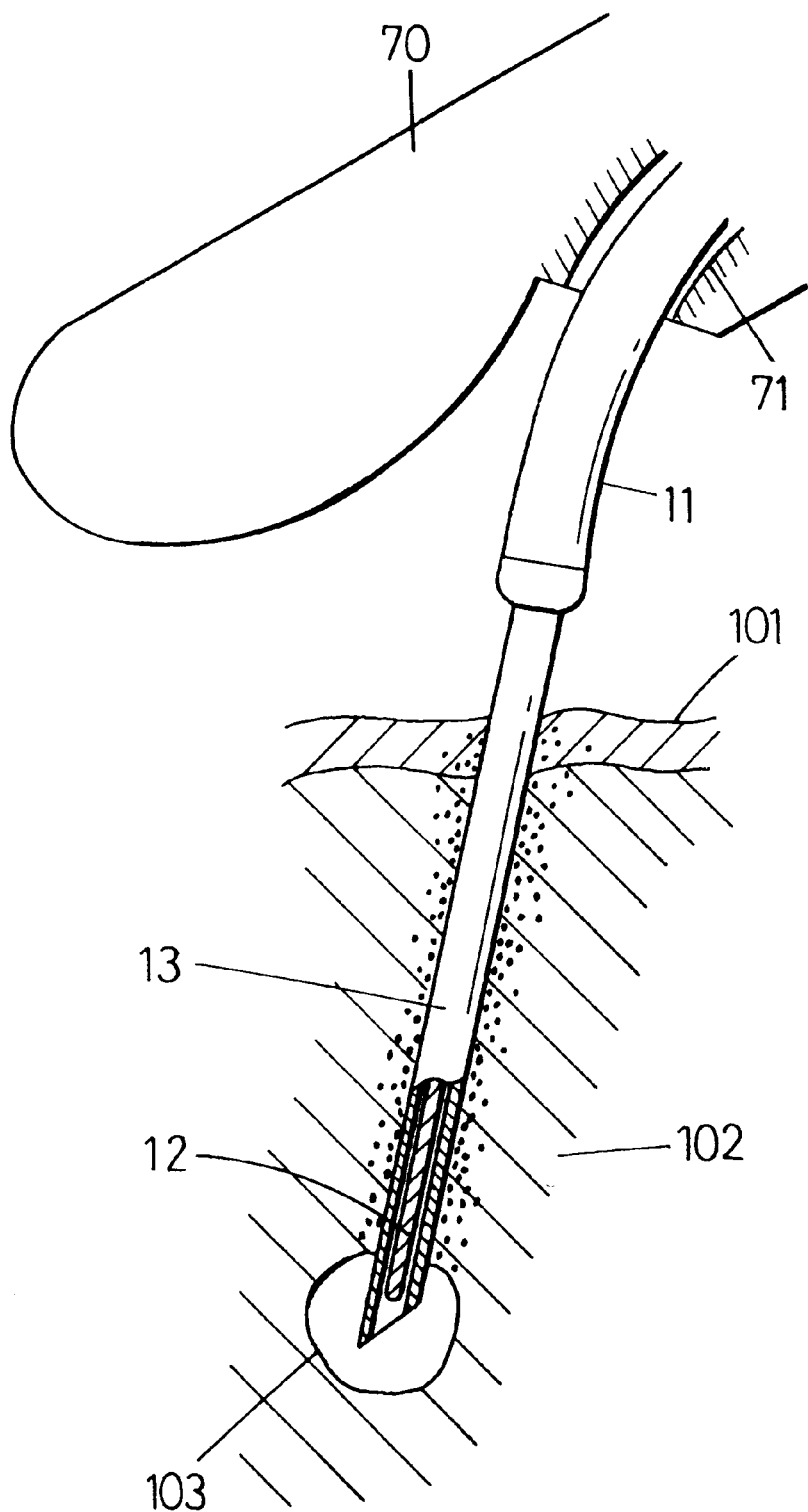
FIG. 21 is a diagram schematically showing the way in which the drainage tube introducer according to the fifth embodiment of the present invention is actually used.

During the puncture treatment, a high-frequency electric current is passed through the tubular needle 13. Consequently, as shown in FIG. 21, organic tissues touching the surface of the tubular needle 13 are cauterized and coagulated. Therefore, the puncture can be readily performed owing to the reduced puncture resistance. Moreover, bleeding is prevented.

It should be noted that to perform puncture, the movable tube 14 is firmly engaged with the operating part body 21, and the whole sheath 11, which is fairly firm, is pushed in to make a hole in tissue. By doing so, puncture can be surely performed. The drainage tube guide wire 12 may be inserted after the puncture. The distal end of the drainage tube guide wire 12 is positioned in the distal end of the tubular needle 13.

Figure 22:
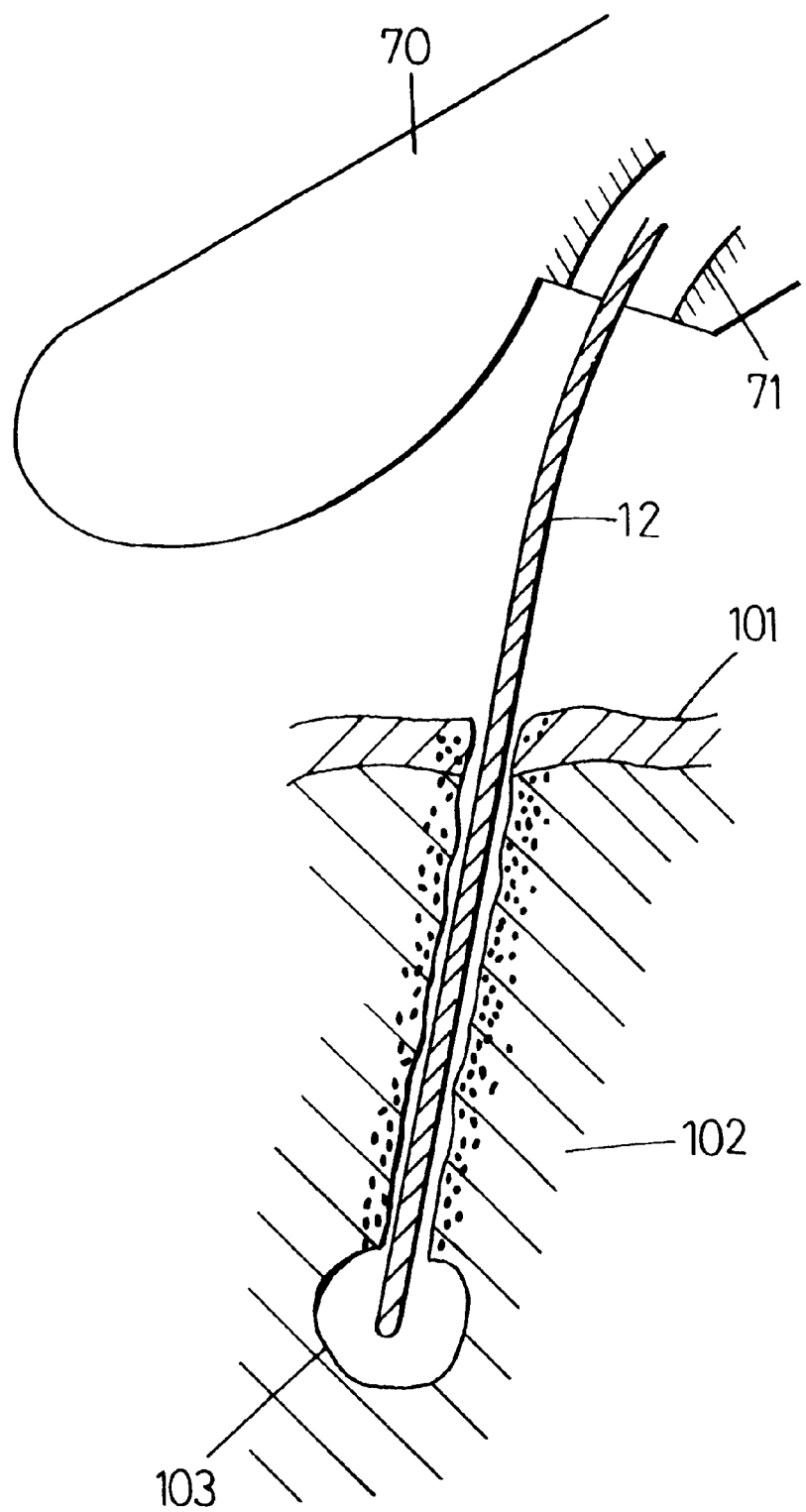
FIG. 22 is a diagram schematically showing the way in which the drainage tube introducer according to the fifth embodiment of the present invention is actually used.

When the distal end of the tubular needle 13 has reached a position in the pancreatic duct 103, as shown in FIG. 22, the drainage tube introducer is drawn out of the instrument-inserting channel 71 of the ultrasonic endoscope 70, with only the drainage tube guide wire 12 left as it is.

Figure 23:
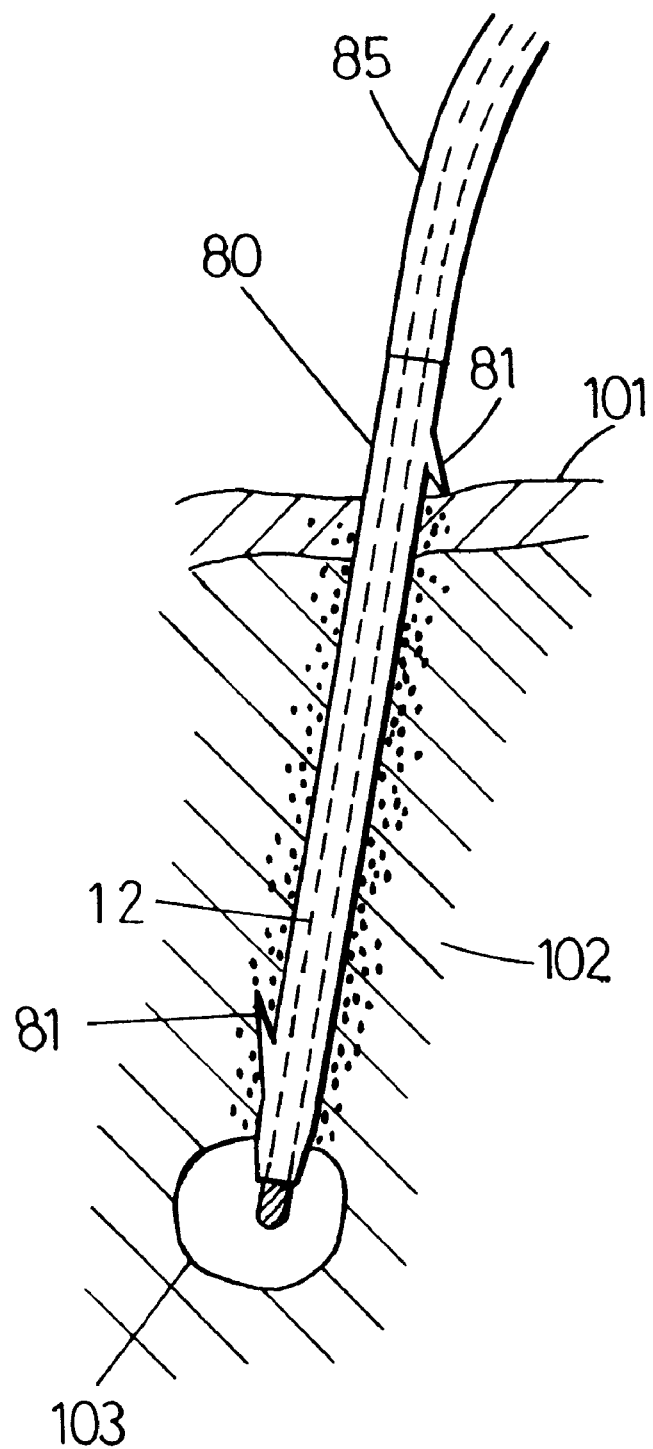
FIG. 23 is a diagram schematically showing the way in which the drainage tube introducer according to the fifth embodiment of the present invention is actually used.

Then, as shown in FIG. 23, a drainage tube 80 is pushed with a pusher 85 by using the drainage tube guide wire 12 as a guide. The pusher 85 is formed from a flexible tube.

When the drainage tube 80 has been positioned such that two ends thereof open into the pancreatic duct 103 and the stomach, respectively, the pusher 85 and the drainage tube guide wire 12 are drawn out of the patient's body. Consequently, the drainage tube 80 is solely left in the body cavity to draw pancreatic juice into the stomach.

Figure 24:
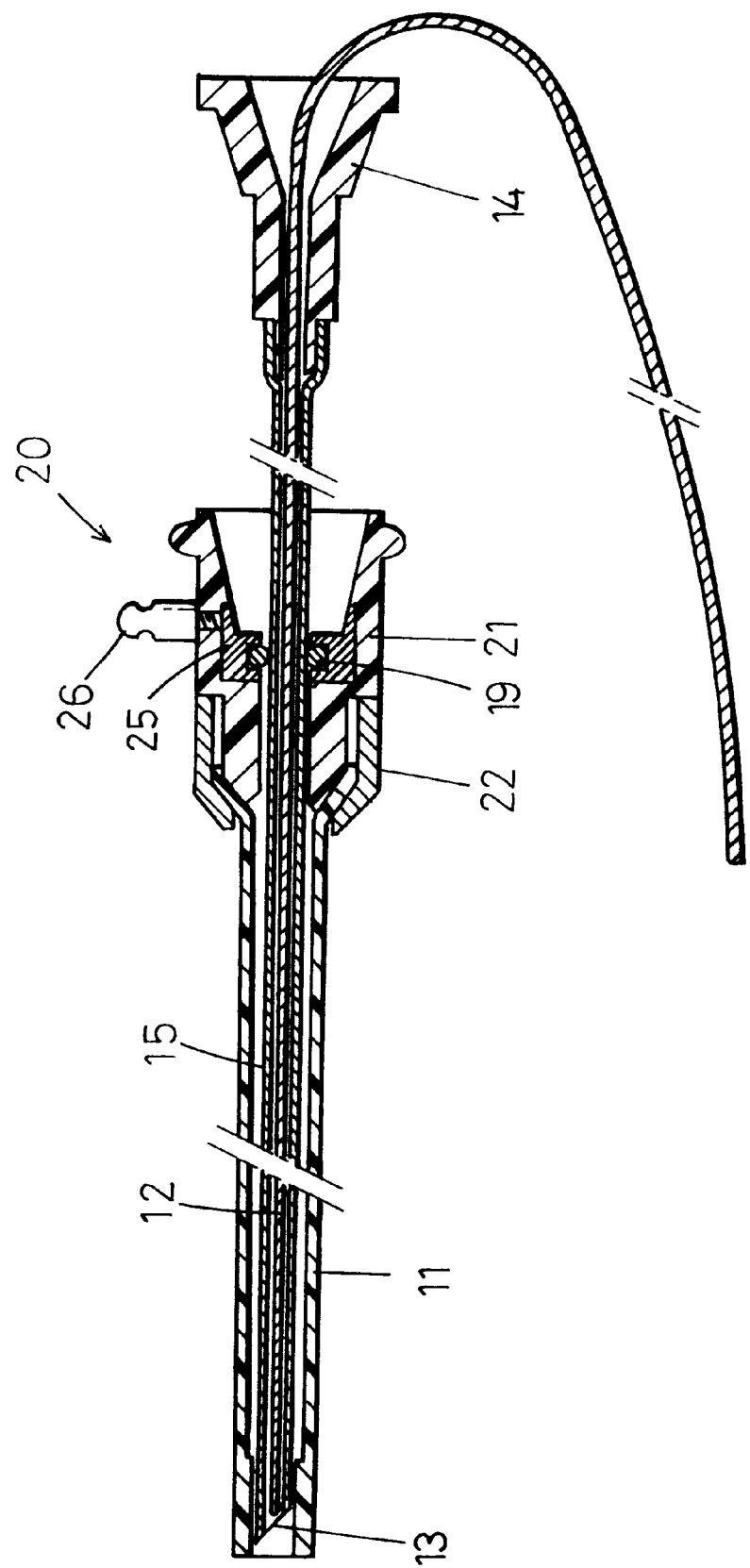
FIG. 24 is a sectional side view of a drainage tube introducer for an endoscope according to a sixth embodiment of the present invention, showing a state wherein a tubular needle as a distal end portion is withdrawn into the distal end of a sheath.

FIG. 24 shows a drainage tube introducer for an endoscope according to a sixth embodiment of the present invention. In this embodiment, an inner tube 15 and a tubular needle 13 are integrally formed from a thin tube of an electrically conductive metallic material, for example, a titanium alloy, a stainless steel, or a super elastic alloy, e.g. a nickel-titanium alloy. A high-frequency electric current is supplied to the tubular needle 13 through the inner tube 15.

The inner tube 15 has a diameter of the order of from 1 millimeter to 2 millimeters. Therefore, it is possible to obtain satisfactory flexibility for practical use by reducing the wall thickness of the inner tube 15.

A sheath 11 is formed from only a flexible electrically insulating tube. The proximal end of the sheath 11 is rigidly connected to an operating part body 21 by a retaining nut 22 screwed onto the operating part body 21.

The operating part body 21 is formed from a non-electrically conductive member. A connecting terminal 26 is provided on a side portion of the operating part body 21. An electric current conducting member 25 is inserted in the operating part body 21. A contact spring 19 is fitted in the electric current conducting member 25 so as to contact the outer peripheral surface of the inner tube 15. The contact spring 19 is formed from a C ring-shaped electrically conductive metal member. Accordingly, the connecting terminal 26 and the contact spring 19 are electrically connected through the electric current conducting member 25.

Consequently, the inner tube 15 can axially move while contacting the contact spring 19 at all times. Thus, a high-frequency electric current is supplied to the tubular needle 13 from the connecting terminal 26 through the electric current conducting member 25, the contact spring 19 and the inner tube 15.

The drainage tube introducer according to the sixth embodiment is used in the same way as in the case of the drainage tube introducer according to the fifth embodiment.

According to the present invention, when a puncture treatment is performed through an endoscope, the inner wall of a body cavity can be punctured with a drainage tube guide wire while cauterizing and coagulating tissues in the body cavity by passing a high-frequency electric current through an electrically conductive exposed portion provided on the outer surface of a part stabbed into the inner wall of the body cavity. Therefore, puncture can be readily performed as far as a deep part without causing bleeding, and a drainage tube can be introduced into the body cavity safely.

While the invention has been described by reference to specific embodiments chosen for purposes of illustration, it should be apparent that numerous modifications could be made thereto by those skilled in the art without departing from the basic concept and scope of the invention.

I claim:

1. A drainage tube introducer for an endoscope, comprising:
   a sheath adapted to be removably inserted into an instrument-inserting channel of the endoscope;
   a drainage tube guide wire axially movably and removably inserted in said sheath;
   a distal end portion of said drainage tube guide wire being projectable from and withdrawable into a distal end of said sheath by an operation conducted at a proximal end of said sheath, so that the projected distal end portion of said drainage tube guide wire can be stabbed into an inner wall of a body cavity; and
   an electric current conducting system provided in said sheath to supply an electric current for cauterization to an electrically conductive exposed portion of said drainage tube guide wire from the proximal end of said sheath;
   wherein said electrically conductive exposed portion is provided on an outer surface of a part of said drainage tube guide wire that is adapted to be stabbed into the inner wall of the body cavity, said electrically conductive exposed portion being formed of an electrically conductive material.

2. A drainage tube introducer according to claim 1, wherein said electrically conductive exposed portion is a distal end portion of said drainage tube guide wire, and at least an outer surface of said sheath is formed from an electrically insulating material.

3. A drainage tube introducer according to claim 2, wherein an overall length of said drainage tube guide wire is at least double an overall length of said sheath, and an electrically insulating covering is provided over an outer surface of at least a portion of said drainage tube guide wire that lies outside said sheath when the distal end portion of said drainage tube guide wire and the distal end of said sheath are aligned with each other.

4. A drainage tube introducer according to claim 2, wherein said electrically conductive exposed portion is a distal end electrode secured to the distal end portion of said drainage tube guide wire, and an outer surface of said drainage tube guide wire, exclusive of said distal end electrode, is covered with an electrically insulating covering.

5. A drainage tube introducer according to claim 4, wherein said distal end electrode has one of a bullet-like shape, a conical shape, and a spherical shape.

6. A drainage tube introducer according to claim 1, wherein said electric current conducting system is said drainage tube guide wire.

7. A drainage tube introducer according to claim 6, further comprising:
   an operating mechanism for conducting the operation whereby the distal end portion of said drainage tube guide wire is projected from and withdrawn into the distal end of said sheath, said operating mechanism being provided at the proximal end of said sheath; and
   a connecting terminal for connection with a power supply that generates an electric current for cauterization, said connecting terminal being provided in said operating mechanism so as to connect electrically with said drainage tube guide wire.

8. A drainage tube introducer according to claim 7, wherein said connecting terminal is provided such that said drainage tube guide wire is locked to and unlocked from said operating mechanism by said connecting terminal.

9. A drainage tube introducer according to claim 8, wherein said drainage tube guide wire has a terminal receiver formed on an intermediate portion thereof to engage with said connecting terminal, said terminal receiver not being provided with an electrically insulating covering, and wherein a whole surface of said drainage tube guide wire, exclusive of said terminal receiver and a distal end portion, is provided with an electrically insulating covering.

10. A drainage tube introducer according to claim 7, wherein said operating mechanism has a cylindrical member connected to the proximal end of said sheath, so that said drainage tube guide wire is axially moved with fingers directly.

11. A drainage tube introducer according to claim 1, wherein a drainage tube is disposed in series at the distal end of said sheath, and said drainage tube guide wire is inserted into both said sheath and said drainage tube.

12. A drainage tube introducer according to claim 1, wherein said sheath has an electrically insulating tube that covers an outer surface of said sheath, and an electrically conductive member as said electric current conducting system that is disposed in said electrically insulating tube, so that an electric current for cauterization is sent to said electrically conductive exposed portion through said electrically conductive member.

13. A drainage tube introducer according to claim 12, further comprising:

an electrically conductive distal end tip secured to the distal end of said sheath, said distal end tip being connected to a distal end of said electrically conductive member, so that an electric current for cauterization is sent to said electrically conductive exposed portion from said electrically conductive member through said distal end tip.

14. A drainage tube introducer according to claim 13, wherein an outer diameter of said distal end tip is smaller than an outer diameter of said sheath.

15. A drainage tube introducer for an endoscope, comprising:

a sheath adapted to be removably inserted into an instrument-inserting channel of the endoscope;

an inner tube axially movably and removably inserted in said sheath;

a drainage tube guide wire axially movably and removably inserted in said inner tube;

a tubular needle formed from an electrically conductive material and provided at a distal end of said inner tube, such that said tubular needle is projectable from and withdrawable into a distal end of said sheath by an operation conducted at a proximal end of said sheath, so that the projected tubular needle can be stabbed into an inner wall of a body cavity; and an electric current conducting system provided in said sheath to supply an electric current from the proximal end of said sheath to said tubular needle for cauterization.

16. A drainage tube introducer according to claim 15, wherein said inner tube is formed from an electrically conductive material as said electric current conducting system, so that an electric current for cauterization is sent to said tubular needle through said inner tube.

17. A drainage tube introducer according to claim 15, further comprising:

an operating mechanism for conducting an operation whereby said tubular needle is projected from and withdrawn into the distal end of said sheath, said operating mechanism being provided at the proximal end of said sheath; and a connecting terminal provided in said operating mechanism to connect with a power supply that generates an electric current for cauterization, said connecting terminal being electrically connected to said electric current conducting system.

* * * * *